United States Patent
Dysarz

[11] Patent Number: 6,099,500
[45] Date of Patent: Aug. 8, 2000

[54] SAFETY NEEDLE CANNULA MODULE THAT IS ACTIVATED BY A SAFETY SYRINGE AND PLUNGER MODULE

[76] Inventor: Edward D. Dysarz, 18 Front St., Rockport, Tex. 78382

[21] Appl. No.: 09/453,393

[22] Filed: Dec. 3, 1999

[51] Int. Cl.⁷ .................................................. A61M 5/00
[52] U.S. Cl. .......................................... 604/110; 604/195
[58] Field of Search ..................................... 604/110, 192, 604/195, 198, 263, 187

[56] References Cited

U.S. PATENT DOCUMENTS

| | | |
|---|---|---|
| 4,973,316 | 11/1990 | Dysarz . |
| 4,978,343 | 12/1990 | Dysarz . |
| 5,019,044 | 5/1991 | Tsao . |
| 5,084,018 | 1/1992 | Tsao . |
| 5,180,369 | 1/1993 | Dysarz . |
| 5,201,710 | 4/1993 | Caselli . |
| 5,267,961 | 12/1993 | Shaw . |
| 5,385,551 | 1/1995 | Shaw . |
| 5,389,076 | 2/1995 | Shaw . |
| 5,891,093 | 5/1999 | Dysarz . |
| 5,935,113 | 8/1999 | Dysarz . |

*Primary Examiner*—John D. Yasko

[57] ABSTRACT

A safety needle cannula module in interchangeable combination with a safety syringe and plunger module, wherein the safety needle cannula module is formed with one of a variety of needle cannula sizes and wherein said safety syringe may be one of a variety of syringe sizes. The safety needle cannula module with needle cannula of desired size is attached to a safety syringe module wherein said safety syringe is a desired size. After medication is injected into a body with the safety needle cannula and the safety syringe, the safety syringe module reacts with the safety needle cannula module and further causes said safety needle cannula to be automatically retracted and disposed within the hollow plunger within said safety syringe module.

10 Claims, 18 Drawing Sheets

SAFETY NEEDLE CANNULA MODULE THAT IS ACTIVATED BY A SAFETY SYRINGE AND PLUNGER MODULE

BACKGROUND OF THE INVENTION

1. Field of the Invention

This invention relates to a single-use syringe for injecting medicine into a patient. More particularly, the invention relates to a safety syringe having a retractable needle cannula that renders the needle cannula harmless after it is used.

2. Background of the Related Art

Many communicable diseases can be spread through the penetration or scratching of the skin by a needle that was previously used by another having the disease. Spreading of the disease in this manner may occur by accident, such as with medical personnel making injections, or it may occur through misuse, such as by intravenous drug users using a previously used needle cannula.

Various syringes have been invented, designed and developed to retract the needle into the syringe or the plunger inside of the syringe. Some of these devices are U.S. Pat. No. 4,973,316 (Dysarz), U.S. Pat. No. 4,978,343 (Dysarz), U.S. Pat. No. 5,180,369 (Dysarz), U.S. Pat. No. 5,267,961 (Shaw), U.S. Pat. No. 5,019,044 (Tsao), U.S. Pat. No. 5,084,018 (Tsao), U.S. Pat. No. 5,385,551 (Shaw), U.S. Pat. No. 5,389,076 (Shaw), and U.S. Pat. No. 5,201,710 (Caselli). These designs have needles which retract at the end of the injection. Most of these designs have not reached the market due, at least in part, to problems associated with the expense of manufacturing, poor reliability or user acceptability. However, even though some of these designs operate poorly or are costly, they have still been commercialized due to the great need in hospitals or clinics for any type of safety syringe.

Most of the existing safety syringe designs allow for automatic retraction of the needle cannula into the plunger barrel of the syringe when the plunger is fully extended into the syringe. The automatic retraction is triggered when the plunger makes physical contact with the distal end of the syringe barrel. Typically, the end of the plunger is provided with a disengagable or sacrificial member at the distar end and the needle cannula is secured by a disengageable or sacrificial member. When the plunger reaches the fully extended position, the physical contact between the plunger and the needle cannula causes activation of the two respective disengageable or sacrificial members. In this manner, the end of the plunger barrel is opened and presented to receive the needle cannula. The needle cannula, no longer secured in position, is biased into the plunger barrel by a spring.

Conventional syringes are typically available in modular systems or kits in which approximately ten different sizes of syringes and approximately ten different sizes of needle cannulas can be used interchangeably. This allows an inventory of twenty items to be used in approximately 100 different combinations in accordance with the present need. However, the safety syringes presently available and described in the above patents are not modular and require stocking of an integral safety syringes for each combination of syringe size and needle cannula size desired, for example 100 different safety syringes. Particularly, in light of the greater cost of these syringes, the cost, distribution and storage of safety syringes is much greater than conventional syringes.

Despite the prevalence of modular conventional syringes, the emergence of a multitude of safety syringe designs and the increasing public outcry for safety syringes, the complexities of the safety syringe mechanisms have limited the number of attempts to design a safety syringe that is modular. Two such attempts include modular syringe tip designs that are combined with a conventional syringe as described in U.S. Pat. No. 5,891,093 (Dysarz) and U.S. Pat. No. 5,935,113 (Dysarz). Compared with the foregoing automatically retracting safety syringes, these two designs can be considered to have safety needle cannula assemblies that are self-contained and manually operated, while being connectable to a conventional syringe with a conventional locking arrangement. While these devices serve the aforementioned need for modularity, the obvious drawbacks to the devices include the manual retraction mechanism and the additional length that the needle cannula assembly adds to the syringe.

Therefore, there remains a need for a modular safety syringe system or kit that provides a selection of syringe modules having various sizes and 2 selection of needle cannula modules having various sizes that can be combined on site to form an automatically retractable safety syringe of a desired configuration. It would be desirable if the automatically retractable safety syringe had similar length and usability as a conventional syringe. It would be further desirable if the used automatically retractable safety syringe was compact and secure against accidental needle sticks.

SUMMARY OF THE INVENTION

The invention provides a kit of components for assembling modular safety syringes. The kit comprises two or more safety syringe modules having different diameters and two or more safety needle cannula modules. Each safety syringe module has a syringe barrel; a safety plunger extending through a proximal end of the syringe barrel, wherein the safety plunger having a plunger barrel, a sliding gasket formed along the perimeter of the plunger barrel near the distal end for sealing the plunger against the interior sidewalls of the syringe barrel, a sealing member covering an opening in the distal end of the plunger barrel, and a rigid member adjacent the sealing member; and a connector formed in the distal end of the syringe barrel. Each of the two or more safety needle cannula modules have a housing having a connector formed at a proximal end of the housing and a cannula passage formed through a distal end of the housing; a needle cannula extending through the cannula passage; a slidable piston flange coupled to the needle cannula; a retaining member securing the slidable piston flange in the proximal end of the housing; and a spring disposed within the housing to bias the slidable piston flange in the direction of the plunger opening from the distal end towards the proximal end. The connectors in the two or more safety syringe modules are sealably securable to the connectors in the two or more safety needle cannula modules. Accordingly, securing any one of the two or more safety needle cannula modules to any one of the two or more safety syringe modules provides alignment of the rigid member of the plunger with the retaining member of the safety needle cannula module and alignment of the slideable piston flange with the sealing member of the plunger.

Preferably, the rigid member of the plunger is an end ridge, possibly sloped. The retaining element is selected from a shear plate, break plate, a friction ring, a sacrificial membrane, or a snapon ring. Where the retaining element is a shear plate or a break plate, it may optionally include first and second concentric notches formed therein, preferably such that the rigid member is aligned to contact the retaining element between the first and second concentric notches. Similarly, the sealing member is selected from a break plate, a friction plug, a sacrificial membrane, a snapon plug. The connectors are selected from threads, luer-loks, or snap-on fittings.

Another aspect of the invention provides an improvement to a medical device having an elongate hollow body; a movable hollow member slidable axially in the body; a retraction mechanism including a needle extending from the body for injecting or collecting fluid, a needle holding member having an unretracted position, a spring for applying retraction force to the needle holding member in a retraction direction, and a retaining element capable of holding the needle holding member against the retraction force provided by the spring; and a cap releasably sealing a passage in the end of the movable hollow member that is positioned within the body; the retaining element being triggered to retaining the needle holding member for retraction of the needle in response to selective movement of the movable member, and the cap being retainingd from the passage of the movable hollow member in response to the selective movement of the movable member. The improvement comprises a sloping end ridge formed on the end of the movable hollow member to contact the retaining element upon selective movement of the movable member. For example, the retaining element may be selected from a break plate, a friction ring, a sacrificial membrane, or an interference fit and may be triggered by failing, sliding, or disengaging. Particularly, the retaining element or cap may be sloped along with the sloping end ridge.

Yet another aspect of the invention provides an improvement to a medical device having an elongate hollow body; a movable hollow member slidable axially in the body; a retraction mechanism including a needle extending from the body for injecting or collecting fluid, a needle holding member having an unretracted position, a spring for applying retraction force to the needle holding member in a retraction direction, and a retaining element capable of holding the needle holding member against the retraction force provided by the spring; and a cap releasably sealing a passage in the end of the movable hollow member that is positioned within the body; the retaining element being triggered to release the needle holding member for retraction of the needle in response to selective movement of the movable member, and the cap being released from the passage of the movable hollow member in response to the selective movement of the movable member. The improvement comprises a spring shield coupled to the needle holding member and extending around the spring, wherein the spring is disposed concentrically around the needle. Preferably, the spring shield is a tube disposed concentrically around the spring, where the spring shield has an outer diameter that is less that an internal diameter of the passage in the movable hollow member.

BRIEF DESCRIPTION OF THE DRAWINGS

So that the above recited features and advantages of the present invention can be understood in detail, a more particular description of the invention, briefly summarized above, may be had by reference to the embodiments thereof which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 1:
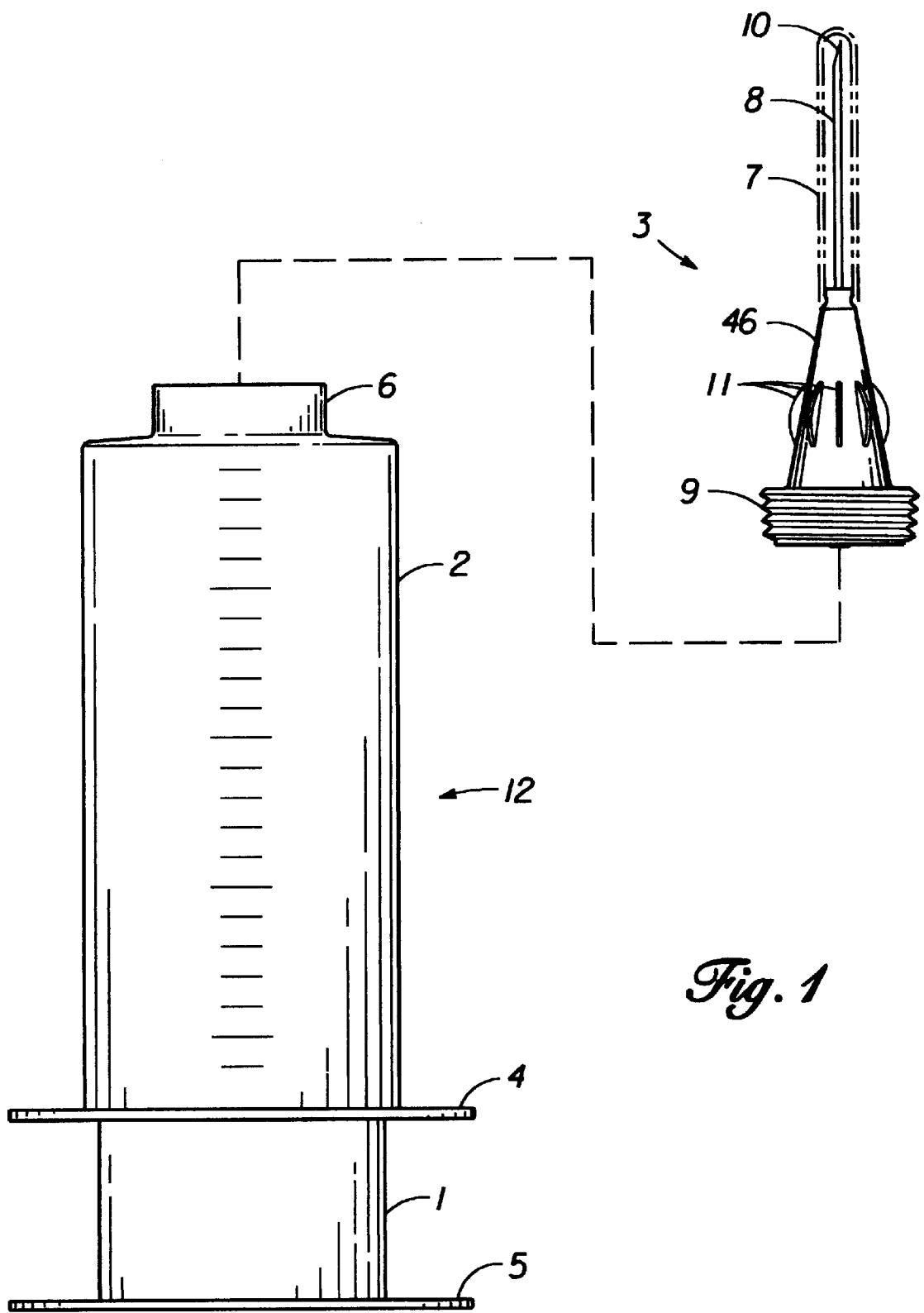
FIG. 1 is an elevation view of the safety needle cannula module and the safety syringe and plunger module.

The present invention provides a modular safety syringe system or kit that provides a selection of safety syringe modules having various sizes and a selection of needle cannula modules having various sizes that can be combined on site to form an automatically retractable safety syringe of a desired configuration. In addition to requiring a common interface between the safety syringe module and needle cannula module, as with conventional modular systems, the present invention also requires and facilitates a specific cooperative relationship between the syringe plunger module and the needle cannula module.

Each safety syringe module of the present invention includes a syringe barrel, a safety plunger extending through a proximal end of the syringe barrel, and a connector formed in the distal end of the syringe barrel. A syringe barrel may be of any length and diameter, as dictated by the volume of fluid to be delivered through the syringe, and will include a connector have a fixed diameter. In systems, sets or kits having a plurality of syringes with different diameters, each syringe should have a connector with a common diameter and a common connection type. For example, three syringe barrels may be provided with diameters of 2, 2.5 and 3 centimeters, respectively, but each of the three syringe barrels should have a connector of the same type, such as threads, and of the same diameter, such as 1.5 centimeters. It should be recognized that in sets having syringes with wide variations in syringe barrel diameter, the set may include a first subset of syringes having a first common connector with a first common diameter and a second subset of syringes having a second common connector with a second common diameter. The present invention contemplates any number of subsets, each subset having the same or different type of connector, and each subset having the same or different connector diameter. It should be recognized that the term "diameter" as used herein shall not be limited to the dimensions of a circular opening, but shall include the dimensions of any shape of opening, for example shapes like squares, triangles, ovals, and rectangles.

The safety plungers of the present invention have suitable lengths and diameters to work in a cooperative relationship inside the syringe barrels. It is anticipated that each syringe of a different diameter will have a corresponding safety plunger of suitable size. The safety plunger has a plunger barrel, a sliding gasket formed along the perimeter of the plunger barrel near the distal end for sealing the plunger against the interior sidewalls of the syringe barrel, and a removable member sealing a central opening in the distal end of the plunger barrel. The safety plunger will also include a lip or similar structure that engages a critical portion of the needle cannula module as described below.

The safety needle module has a connector that is designed to be coupled to the connector on the safety syringe module. These connectors may be of various types, including but not limited to male/female threads, snap-on, and luer-lok tips. In systems, sets or kits having a plurality of safety needle modules with different cannula diameters, gauges, types or lengths, each safety needle module should have a connector with a common diameter and a common connection type. For example, three safety needle modules may be provided with, but not limited to, 16G, 20G and 30G cannulas, respectively, but each of the three modules should have a connector of the same type, such as male threads, and of the same diameter, such as 1.5 centimeters. Furthermore, it should be recognized that the safety needle modules will preferably all have the same type of connector, such as male threads or the male portion of a luer-lok, and the safety syringe modules will preferably all have the same type of connector that mates with the needle module connector, such as female threads of the female portion of a luer-lok. In the case where there are subsets of syringes having connectors with different diameters, then there will also be subsets of safety needle modules having connectors with the same mating diameters.

The safety needle module includes a housing having the connector at the proximal end and a cannula passage through the distal end. A needle cannula coupled to a slidable piston flange extends through the cannula passage. The slidable piston flange is secured to the housing by a disengageable, sacrificial or retaining member. A spring is disposed within the housing to bias the slidable piston flange, and consequently the needle cannula, away from the distal end towards the proximal end. The spring surrounds the needle cannula and is maintained in a biased or spring loaded condition between the distal end of the housing and the slidable piston flange. It is important that the spring provide sufficient force to move the needle cannula into the plunger barrel upon release, but the spring should not be so strong as to fatigue or cause failure to the disengageable or sacrificial member that secures the slidable piston flange to the housing.

It should be recognized that the disengageable or sacrificial members in the safety plunger and in the safety needle module may take many forms, including plates that can fail, break or shatter as described in U.S. Pat. No. 5,180,369 (Dysarz) incorporated by reference herein, frictionally engaged retaining rings and plugs as described in U.S. Pat. No. 5,285,551 incorporated by reference herein, sacrificial membranes, interference fits, and the like.

It is a critical aspect of the invention that a rigid component of the safety plunger is disposed at an appropriate position to engage and actuate the retaining member in the safety needle module and that a rigid component of the safety needle module is disposed at an appropriate position to engage and actuate the sealing member in the safety plunger. Since syringes typically have cylindrical barrels, although they could just as well have any shaped cross-section, the positions of the two rigid components, the sealing member and the retaining member can be described in terms of concentric members having a specific radial distance from the axial centerline of the needle cannula. While two of the concentric members are in the safety plunger and the other two concentric members are in the needle module, the members must achieve a standard, fixed or consistent cooperative relationship when assembled and, consequently, must have standard radii or other dimension and threads specified for each of the two rigid components, the sealing member and the retaining member. For any given set or subset of safety syringe modules and safety needle modules, these radii must be the same regardless of the syringe diameter or the cannula gauge. In other words, the size and alignment of the members accounting for the automatic retraction must be consistent in order for the retraction to occur.

Consistent alignment of the members, including alignment of a rigid plunger member with the needle retaining member and alignment of the rigid safety needle member with the plunger sealing member, can be achieved either by (a) using a constant plunger barrel diameter regardless of syringe diameter, or (b) using plunger barrels having a diameter just smaller than the syringe barrel, but having a diameter at the distal end that is reduced, or perhaps even increased, to form or achieve the fixed radii of the rigid plunger component. The former option is less desirable, because the plunger barrel could wobble from side to side and the gasket member would not receive as much physical support.

Now referring to the Figures, FIG. 1 is an elevation view of the system or kit of the present invention. The system includes a separate safety syringe module and a safety needle cannula module. The safety syringe module includes a safety plunger 1 and a syringe module 2. A syringe connector 6 is shown formed in the distal end of the syringe barrel 2, preferably forming a set of female threads. Finger tabs 4 are shown at the proximal end of the syringe barrel 2. The syringe barrel 2 is a hollow elongated barrel with an inside surface and an outside surface. The safety plunger 1 is also an elongated barrel with an inside surface and an outside surface. The safety plunger is shown disposed within the syringe barrel 2 with a thumb flat 5 shown at the proximal end of the safety plunger.

The safety needle cannula module 3 is shown with a needle cannula 8 extending from the distal end of a housing 46 having male threads that are attachable to the female threads formed on the syringe connector 6 of the syringe barrel 2. A needle protector cap 7 is shown removeably fixed to the distal end of the safety needle cannula module 3 to prevent any contamination to the needle cannula 8 and to further protect the needle cannula point 10. Gripping members or wings I 1 are also shown formed on the exterior of the safety needle cannula module 3 to allow for ease of gripping the safety needle cannula module 3 while threading the safety needle cannula module 3 to the syringe connector 6 of the safety syringe module.

Figure 2:
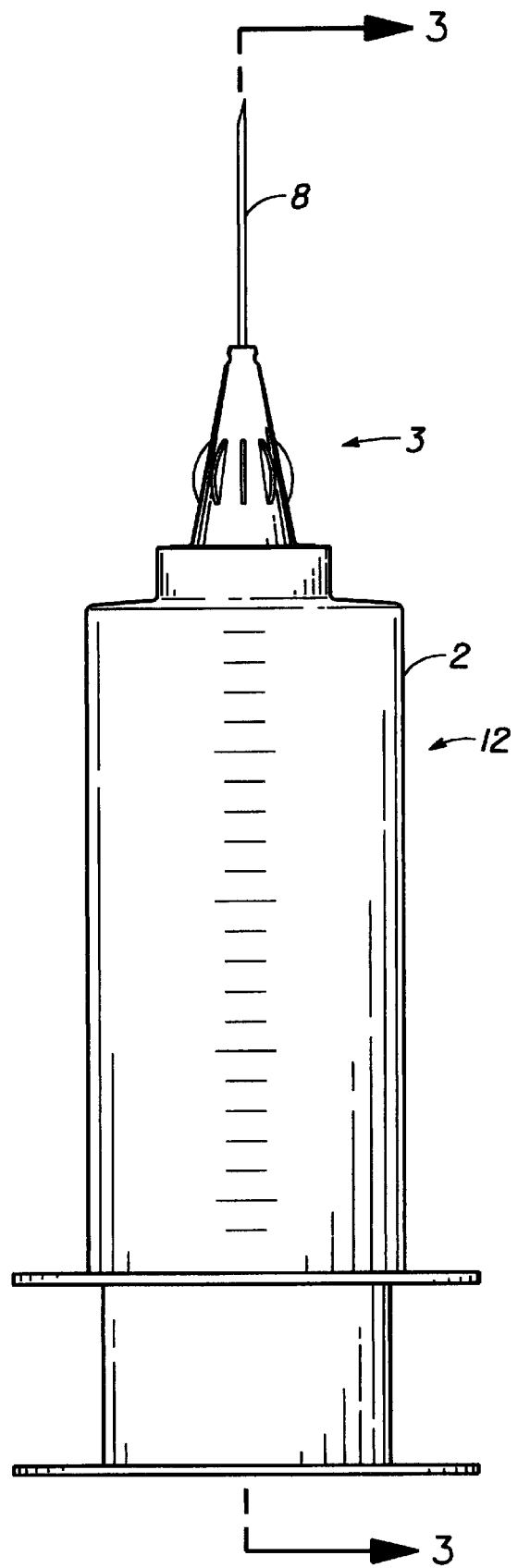
FIG. 2 is an elevation view of the safety needle cannula module fixed to the safety syringe and plunger module.

FIG. 2 is an elevation view of the safety needle cannula module 3 suitably attached to the safety syringe module 12 via a threaded connection. The needle protector 7 that was protecting the needle cannula 8 in FIG. 1 has been removed and the assembled device consisting of the two modules 3, 12 is ready to be used.

Figure 3:
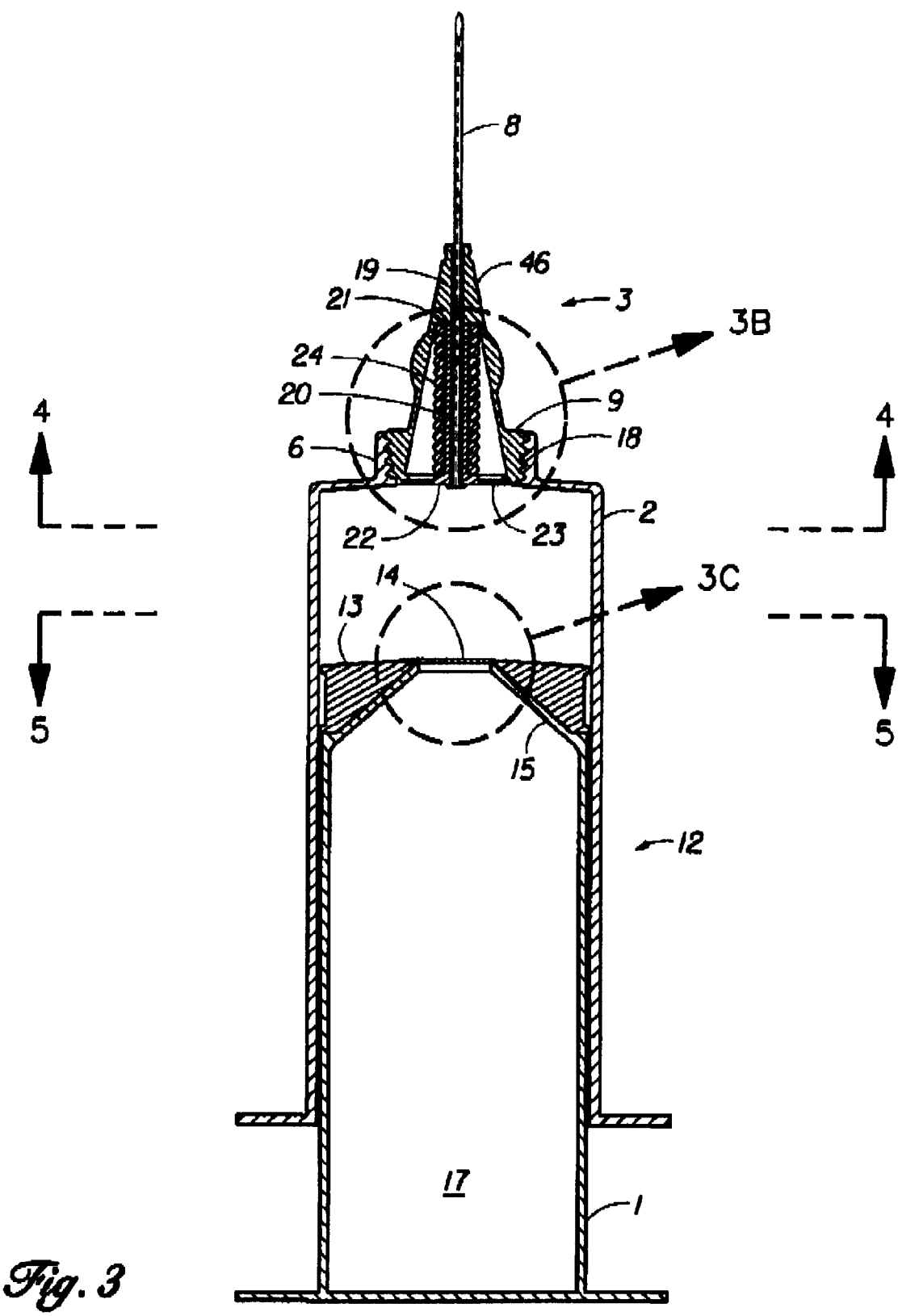
FIG. 3 is a section elevation of the safety needle cannula module shown fixed to the safety syringe module.

FIG. 3 is a section elevation of the device, as taken through FIG. 2. The safety plunger 1 is shown formed into a frustoconical surface or other tapered surface 15 at the distal end and a sliding gasket 13 is shown having syringe sealing surfaces. The plunger sealing member 14 is shown in this embodiment as a push in barrier borne on the distal end of the cone 15, where the cone 15 has a diameter matching up with a retaining member 23, shown in this embodiment as a point load plate. The sealing member 14 has sufficient strength to withstand typical hydraulic pressures that can be exerted on it while the plunger is thrusting medicament into a body, however, the sealing member will fail or disengage and be pushed into the plunger cavity 17 whenever the force applied on the thumb flat is provided as a concentrated load applied to the sealing member. In the embodiment where the sealing member is a push in barrier, it is preferable that a point load or an eccentric load is applied to the barrier.

The term "concentrated load", as used herein, means a load or force that is directed at a specific member or portion of a member, as opposed to a load of similar magnitude that is spread out over a large surface area. For example, when a syringe has been filled with medicine, the advancing plunger applies a load to the fluid in the syringe that pushes against all surfaces exposed to the fluid. By contrast, when all the medicine has been dispensed, the rigid member of the advancing plunger makes contact with a portion of the retaining member such that the entire amount of force applied to the thumb flat is directed against that portion of the retaining member. It is this latter load that is refered to as a "concentrated load."

The housing 46 has a threaded connector 9 formed on the proximal end of the needle cannula module 3 and the connector 9 is shown suitably meshed and fixed to the female threads 18 formed on the syringe connector 6, shown in this embodiment as an extended collar. The connection formed between the threads of the two modules should be a fluid (gas and liquid) tight connection. A needle passage 19 is shown formed in the distal end of the safety needle cannula module 3 that allows the needle cannula 8 to retract into the inside of the safety plunger 1 without oscillating transversably.

The needle cannula 8 is shown suitably fixed to a slideable piston 20 by adhesive or friction or some other means by design choice. The distal end of the slideable piston 20 is near the cannula flat 21. A slideable piston flange 22 is formed near the proximal end of the slideable piston 20. A retaining member 23, shown in this embodiment as a point load plate, secures the proximal end of the slideable piston 20 to the housing 46. A biased spring 24 is compressed between the cannula flat 21 and the slideable piston flange 22 in order to bias the slideable piston flange, and consequently the needle cannula, toward the plunger barrel.

The point load plate 23 is shown formed on the slideable piston flange 22 and extends near the inside surface of the housing 46 of the safety needle cannula module 3. The point load plate 23 is suitably fixed to the inside surface of the safety needle cannula module by adhesive, plastic, welding, friction, snap-on or some other suitable means by design choice.

Figure 3A:
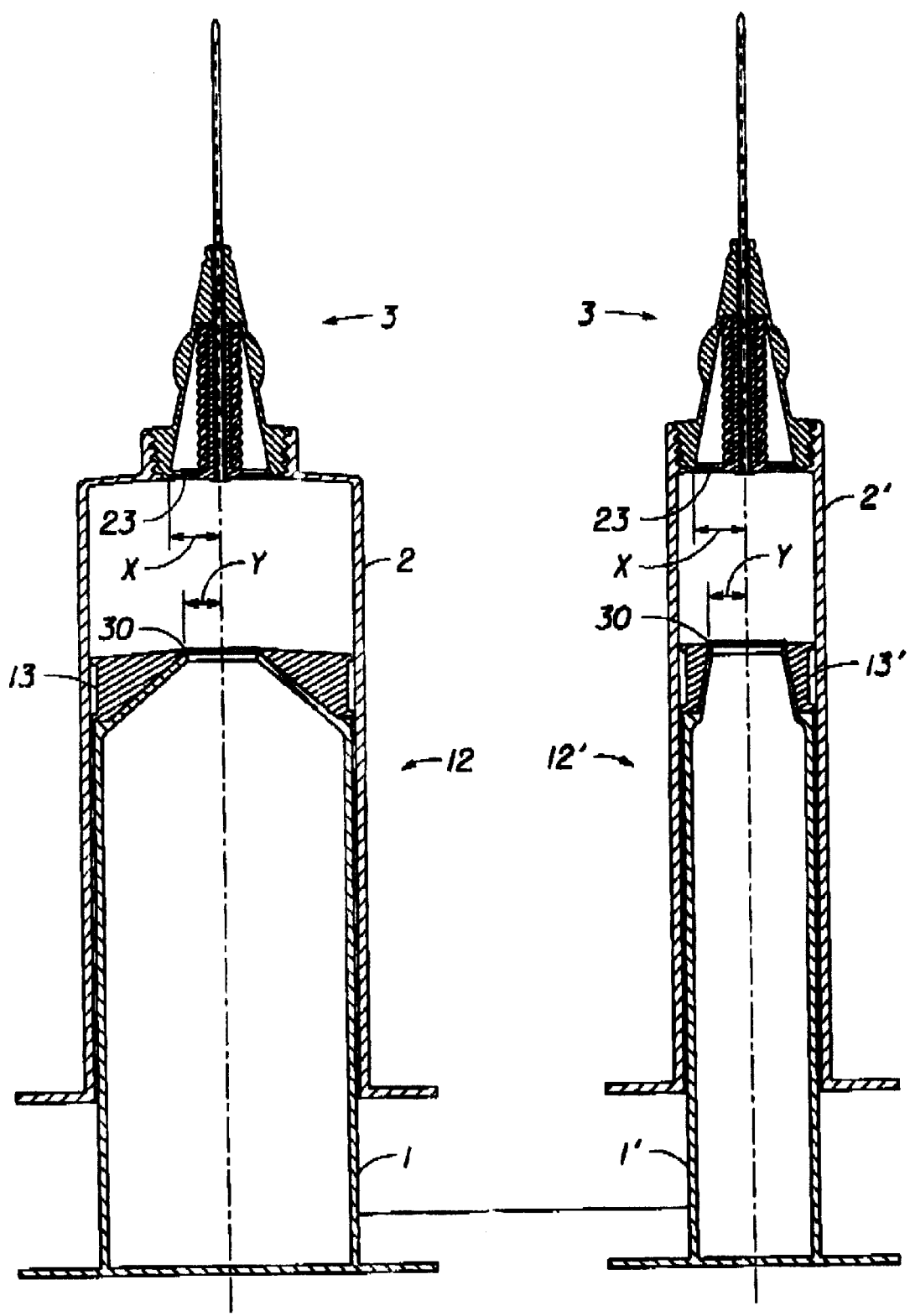
FIG. 3A is a section elevation of two safety syringes having different syringe barrel diameters.

FIG. 3A is a section elevation of two safety syringe modules 12, 12' as might be provided as part of a kit of components for on site assembling of automatically retractable safety syringes. The two safety syringe modules 12, 12' have syringe barrels 2, 2' with different diameters for drawing and injecting different quantities of fluid. Despite the different syringe barrel diameters, each safety syringe module 12,12' is coupled through the same type (here, common pitch and style threads) and same size (here, diameter x and length) of connectors to a safety needle cannula module 3. The diameters of the safety plungers 1, 1' and the gaskets 13, 13 are dictated by the different diameters of the syringe barrels 2, 2'. However, according to the present invention, even though the plunger diameter changes with the syringe diameter, the safety plunger 1 must maintain a rigid component or end ridge 30 at a fixed radial distance y from the axial centerline of the syringe to be in alignment with the retaining member 23 of the safety needle cannula module 3. Similarly, the slideable piston flange of the needle cannula module 3 must be maintained in alignment with the sealing member of the plunger 1.

Figure 3B:
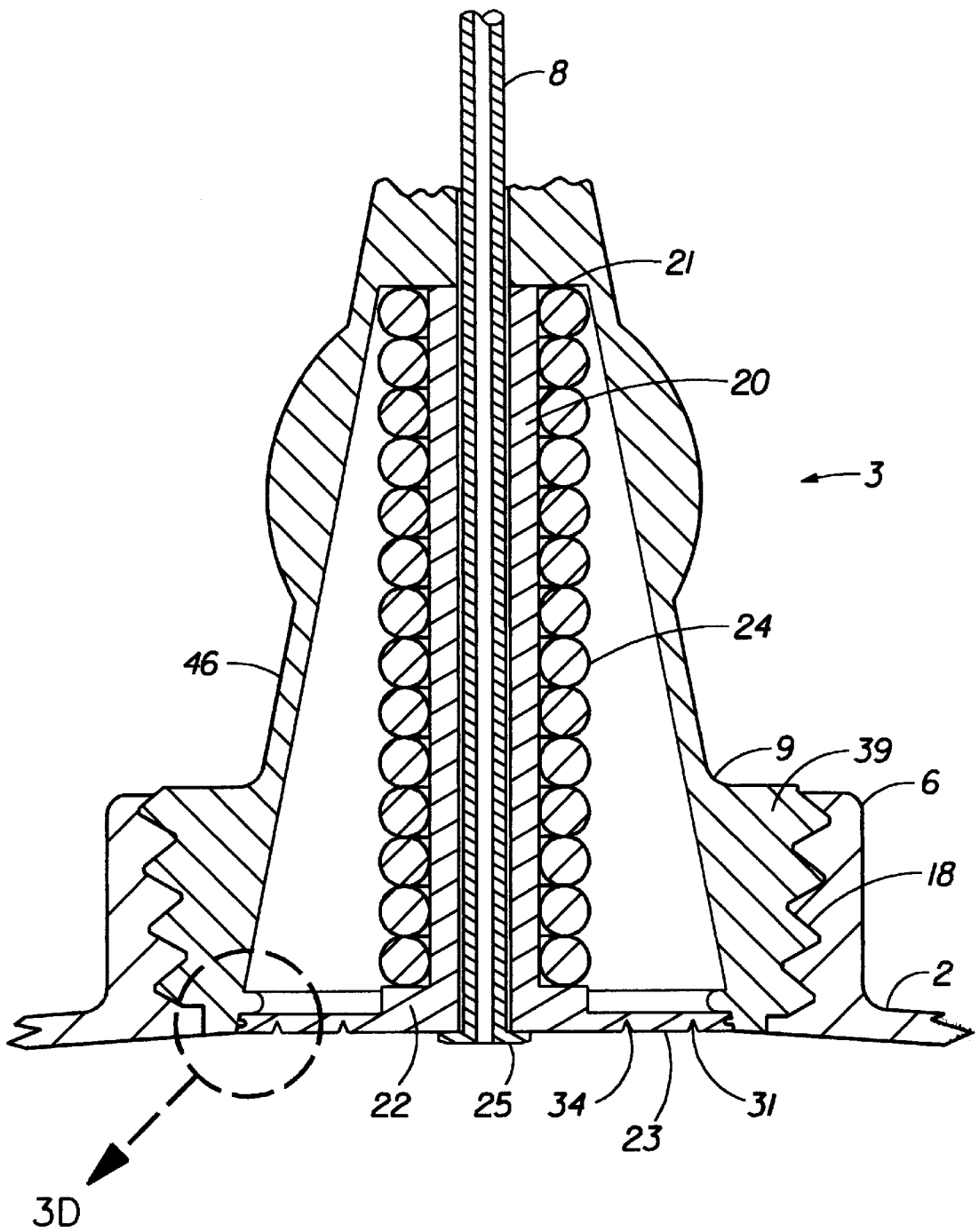
FIG. 3B is an enlarged section elevation of the needle cannula module.

FIG. 3B is an enlarged section elevation as taken from FIG. 3 showing more clearly the safety needle cannula module 3. The safety needle cannula module 3 has a connector 39 suitably fixed or assembled to the syringe connector 6 formed on the distal end of the syringe barrel 2, shown here as male threads 39 on the connector 9 mating with female threads 18 formed on the syringe barrel 2. The biased spring 24 is shown compressed between the slideable piston flange 22 and the cannula flat 21. The needle cannula 8 is shown suitably secured to the slideable piston 20. The proximal end of the needle cannula 8 is shown with a cannula flange 25. The slideable piston flange 22 is formed on the proximal end of the slideable piston 20, allowing the biased spring 24 to thrust against the slideable piston flange 22.

In one preferred embodiment, the slideable piston flange 22 is held, secured or fixed to a point load plate 23. The point load plate 23 is preferably provided with a first break away notch 31 and a second breakaway notch 34 formed in the proximal side of the point load plate 23. The breakaway notches could be formed on the distal side of the point load plate 23 or the proximal side of the point load plate 23 by design choice. The point load plate 23 is designed to fail when a point load is applied or when a concentrated load is applied to the necessary location. It should be recognized that the failure mode of the point load plate may include breaking, shattering, tearing or otherwise releasing the slideable piston flange. Most preferably, the point load plate 23 is suitably fixed to the inside surface of the safety needle cannula module 3 with a snap on fluid and gas tight connection, although it should be recognized that adhesives or other means could be utilized to secure applied by design choice.

Figure 3C:
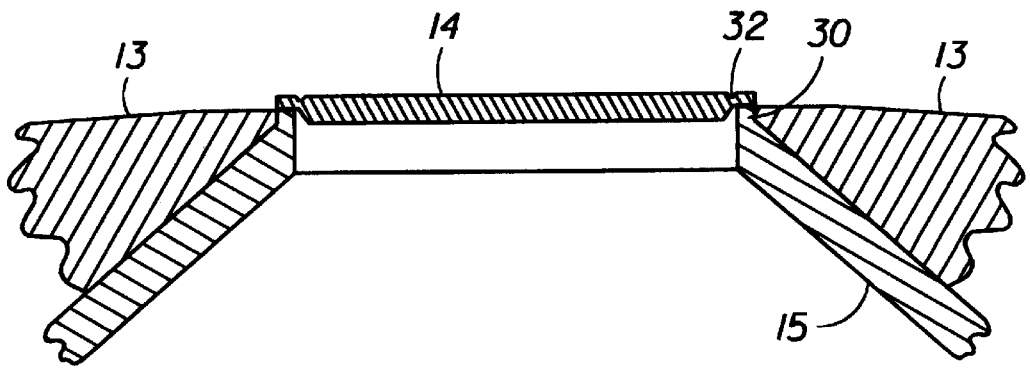
FIG. 3C is an enlarged section elevation of the first end of the plunger module.

FIG. 3C is an enlarged section elevation of the push in barrier 14 secured to the end ridge 30 at the first end of the rigid plunger member or cone 15. While the barrier is shown attached at the distal-most surface of the end ridge, it should be recognized that the barrier may be attached to an inner surface of the end ridge 30, the cone 15 or another surface of the plunger. Further, while it is preferred that the end ridge 30 or a portion of the barrier 14 extend distally from the end of the sliding gasket, it is anticipated that the gasket could be made compressible so that the "end ridge" is normally recessed but, upon compression of the gasket, presents itself to contact the retaining member.

The sliding gasket 13 is shown attached to the plunger, preferably along the outer surface of the cone 15. The push in barrier 14 is shown with a break off notch 32 that is circumferential in this particular figure, however, break off notches could be included in any number, pattern or dimension. Specifically, the break off notch 32 could bisect the push in barrier 14 in various directions by design choice. The push in barrier 14 should be strong enough to withstand any hydraulic pressure applied to its distal (medicament exposed) side, but should be unable to withstand any point loading, concentrated load or eccentric load directed on the barrier without breaking away from the end ridge 30. Where any unequally applied load is generated on the push in barrier 14, the push in barrier will break off at or near the break of notch 32. Again, it should be recognized that the failure mode of the push in barrier may include breaking, shattering, tearing or otherwise rendering access to the plunger cavity 17.

Figure 3D:
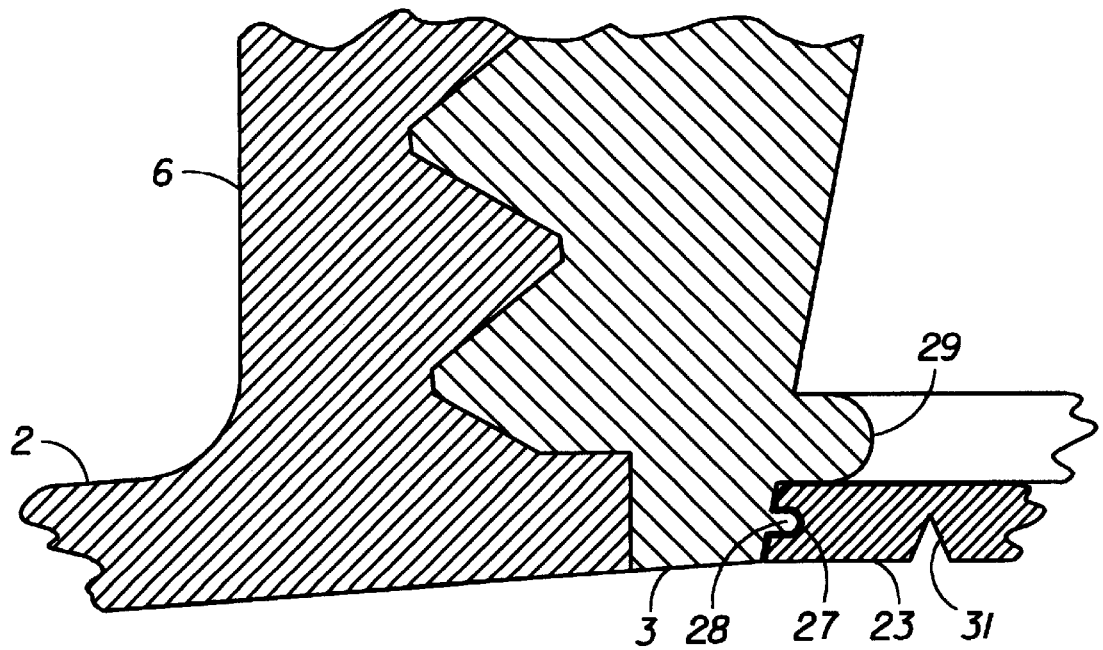
FIG. 3D is an enlarged section elevation of the threaded connection between the safety needle cannula module and the syringe module.

FIG. 3D is an enlarged section elevation of the snap on connection as taken through FIG. 3B. The point load plate 23 is shown with a snap on channel 27 formed at the outer circumference of the plate. A snap on rib 28 is shown formed on the inside circumference essentially near the proximal end of the safety needle cannula module 3. A backing ridge 29 is shown as another means of securing the point load plate 23 in position. Part of the syringe connector 6 and syringe barrel 2 are shown for reference.

Figure 4:
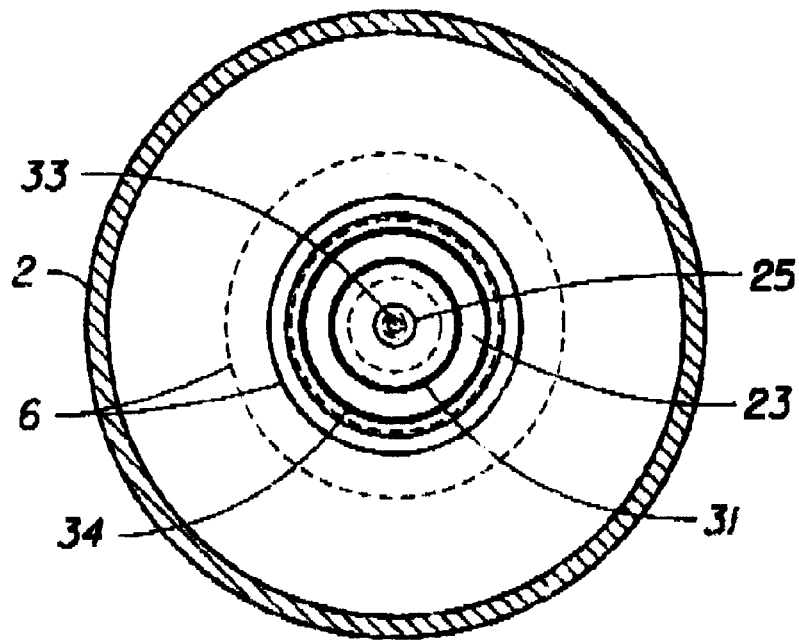
FIG. 4 is a section view of the safety needle cannula module and the safety syringe module as taken through FIG. 3.

FIG. 4 is a section plan view as taken through FIG. 3. The syringe barrel wall 2 is shown at the outer periphery and the outside diameter of the syringe connector 6 is shown as a hidden (dashed) line. The inside diameter of the syringe extension 6 is shown as a solid line for reference purposes. The first break away notch 31 and the second break away notch 34 are part of the point load plate 23 and are shown around the cannula flange 25. The cannula 33 is shown at near the cannula flange 25.

Figure 5:
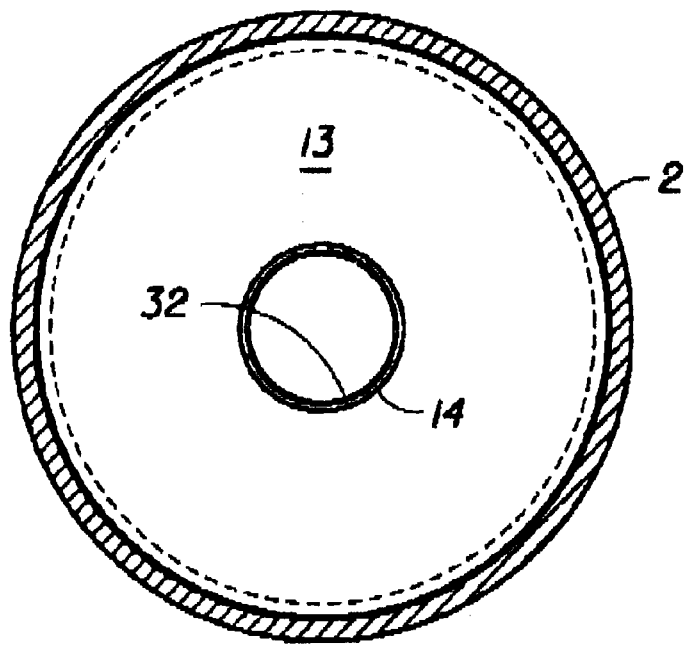
FIG. 5 is a section view of the safety syringe module and a plan view of the safety plunger module within the safety syringe module.

FIG. 5 is another section elevation as taken through FIG. 3. Here, the break off notch 32 is shown on the inside and the outer periphery of the push in barrier is shown around the break off notch 32. The sliding gasket 13 is shown rubbing on the inside surface of the syringe barrel 2.

Figure 6:
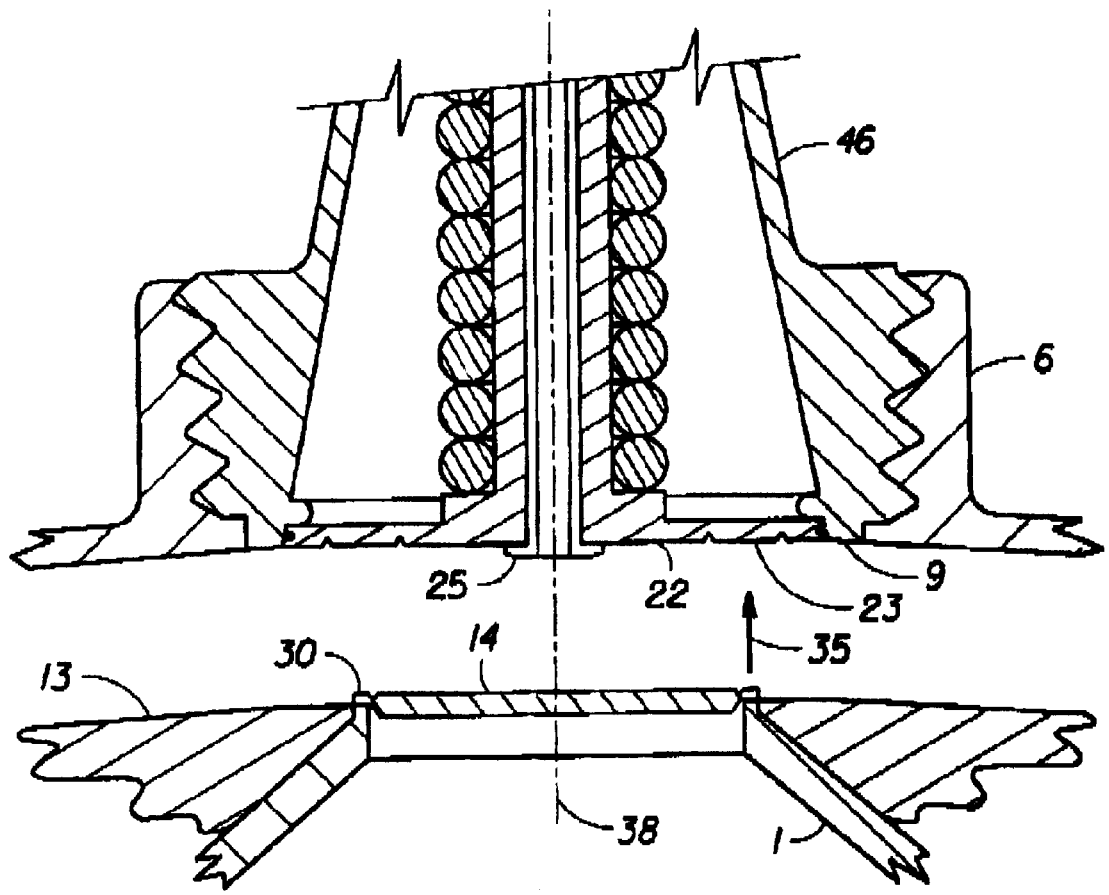
FIG. 6 is a section elevation of the safety plunger module moving toward the safety needle cannula module.

FIG. 6 is another enlarged section elevation of the safety plunger 1 in the proximity of, and being moved toward, the safety needle cannula module 3. As shown, the safety plunger 1 is moving in a closing direction 35 toward the distal end of the syringe barrel. The rigid component or end ridge 30 is moving toward the point load plate 23 between the connector 9 and the slideable piston flange 22. The push in barrier 14 is also moving into the slideable piston flange 22 and the cannula flange 25. The exposed side of the cannula flange 25 could be flush with the piston flange 22 by design choice. A centerline 38 is shown for reference purposes.

Figure 7:
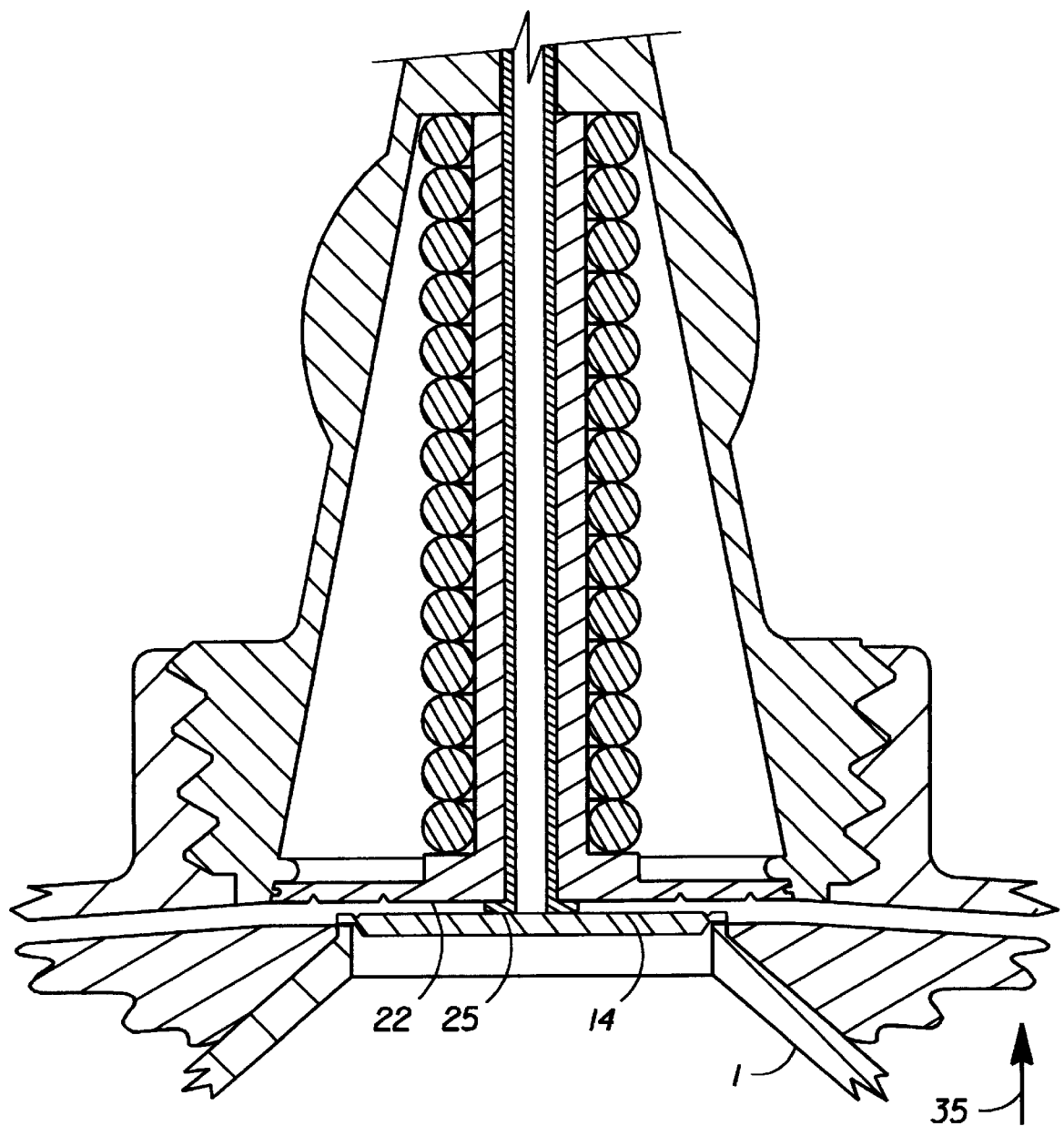
FIG. 7 is a section elevation of the first end of the safety plunger module touching the safety needle cannula module.

FIG. 7 is a section elevation of the distal side of the push in barrier 14 thrusting into the proximal side of the cannula flange 25 while continuing to move in a closing direction 35.

If the cannula flange 25 were flush with the slideable piston flange 22, the distal side of the push in barrier 14 would first come into contact with the proximal side of the slideable piston flange. In either case, the result is substantially the same.

Figure 8:
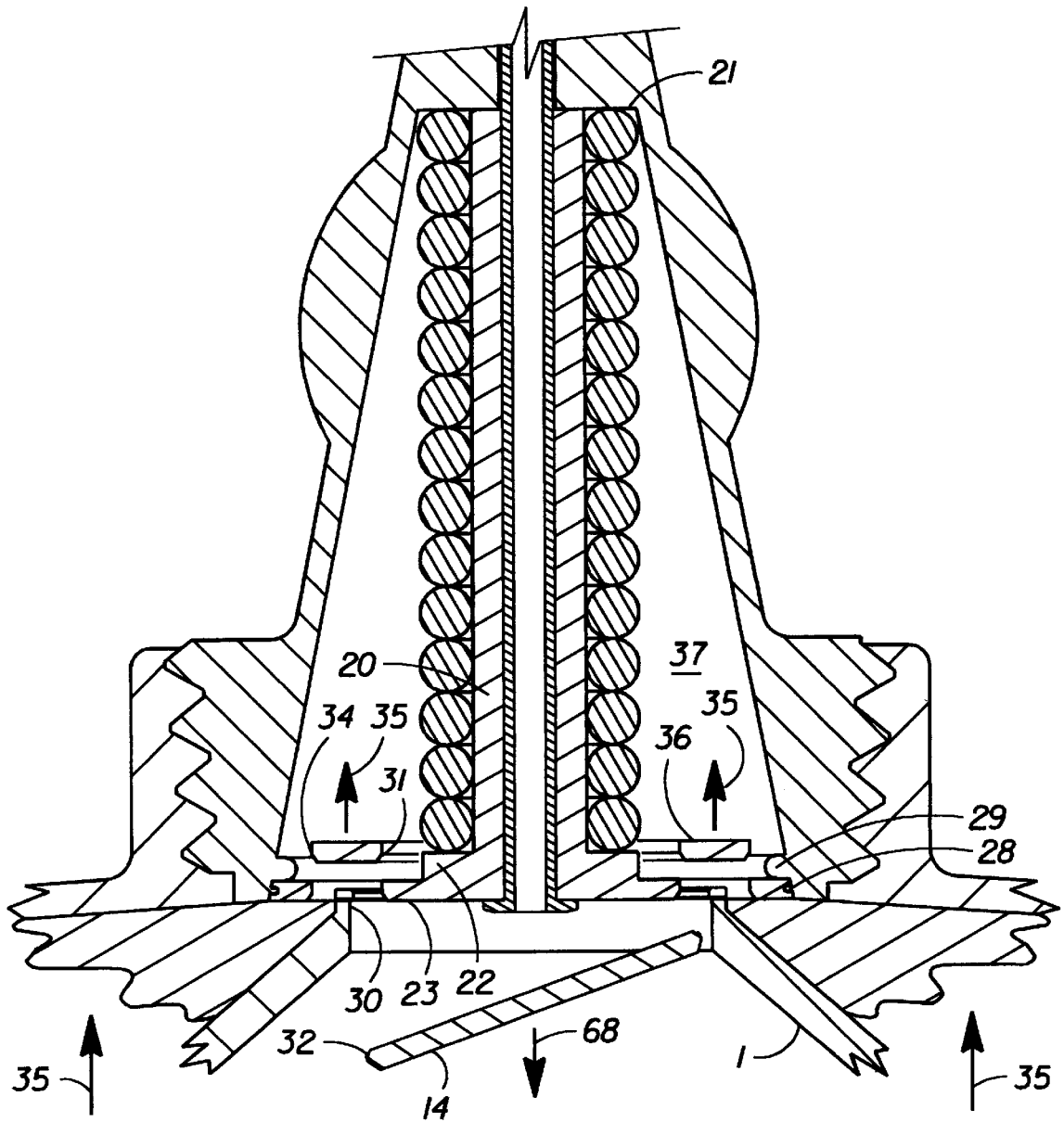
FIG. 8 is a section elevation of the safety needle cannula module point loading the first end of the plunger module.

FIG. 8 is a section elevation view of the break away ring 36 being disengaged from the point load plate 23. The breakaway ring 36 is defined by the first break away notch 31 and the second breakaway notch 34 formed in the point load plate 23. As the end ridge 30 is thrust into the point load plate 23, the plate is supported on the outside periphery by the snap on rib 28 and the backing ridge 29 thereby not allowing any deflection along the outside periphery of the point load plate 23. The point load plate 23 is also supported near the center of the point load plate by the slideable piston flange 22. The slideable piston flange 22 is supported by the slideable piston 20 which, in turn, has a distal end supported by the cannula flat 21 to prevent any deflection between the slideable piston flange 22 and the point load plate 23. Because of this support and the load applied by the end ridge, the point load plate fails at the first break away notch 31 and the second break away notch 34, thereby forming the break away ring 36 which is thrust into the safety needle cannula module chamber 37. As the break away ring 36 is thrust into the safety needle cannula module chamber 37, the slideable piston flange 22 and the slideable piston 20 are thrusting into the push in barrier with a point load or a concentrated load thus causing break off notch 32 formed in the push in barrier 14 to fail and allowing the push in barrier to be thrust in an inward direction 68 into the inside of the safety plunger 1.

Figure 9:
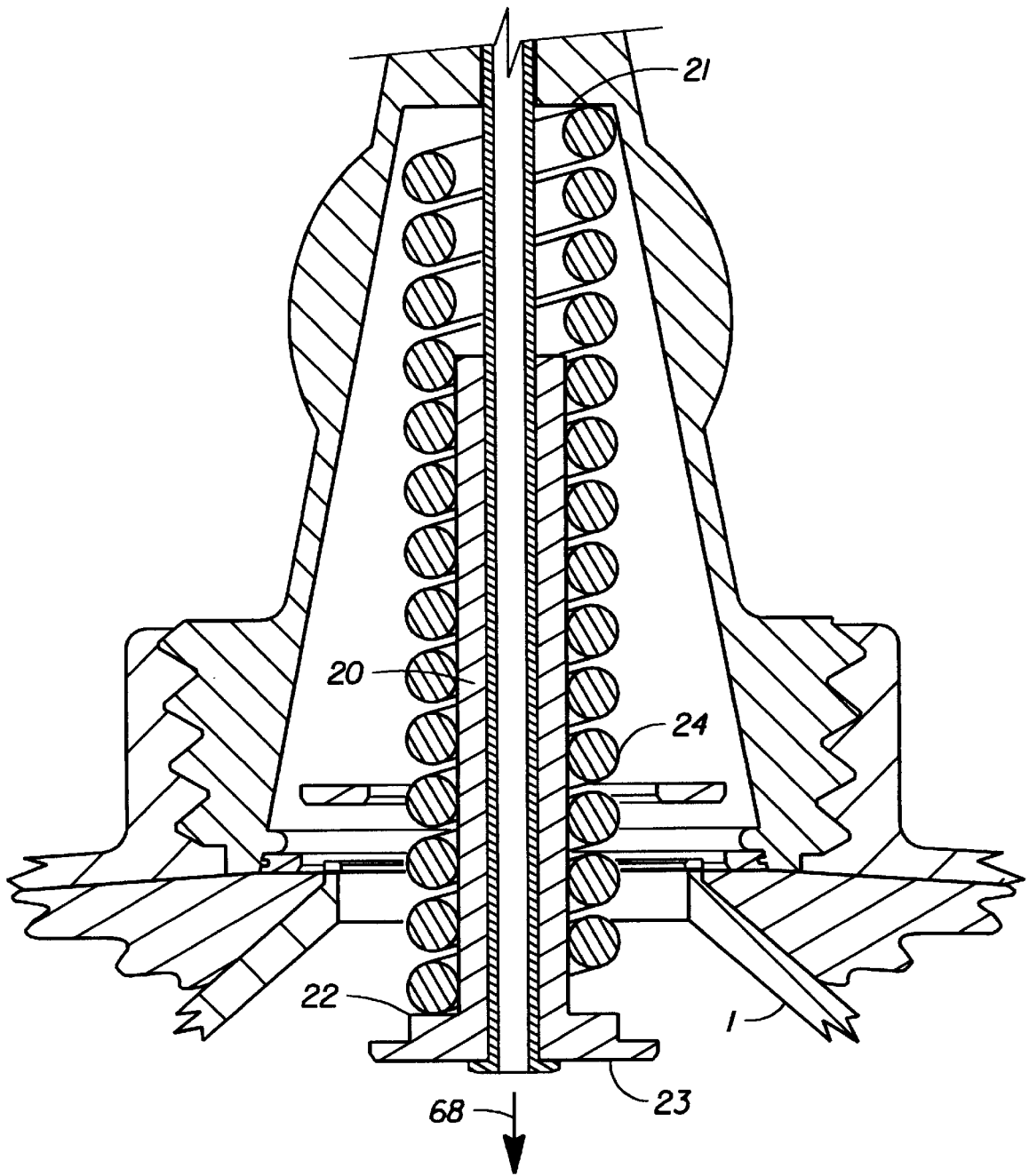
FIG. 9 is a section elevation of the slideable piston and needle cannula thrusting into the plunger module.

FIG. 9 is a section elevation view of the slideable piston flange 23, and the slideable piston 20 being thrust in an inward or proximal direction 68 into the inside of the safety plunger module 1 by the biased spring 24 having a distal end that is thrusting on the cannula flat 21 and a proximal end thrusting on the slideable piston flange 22.

Figure 10:
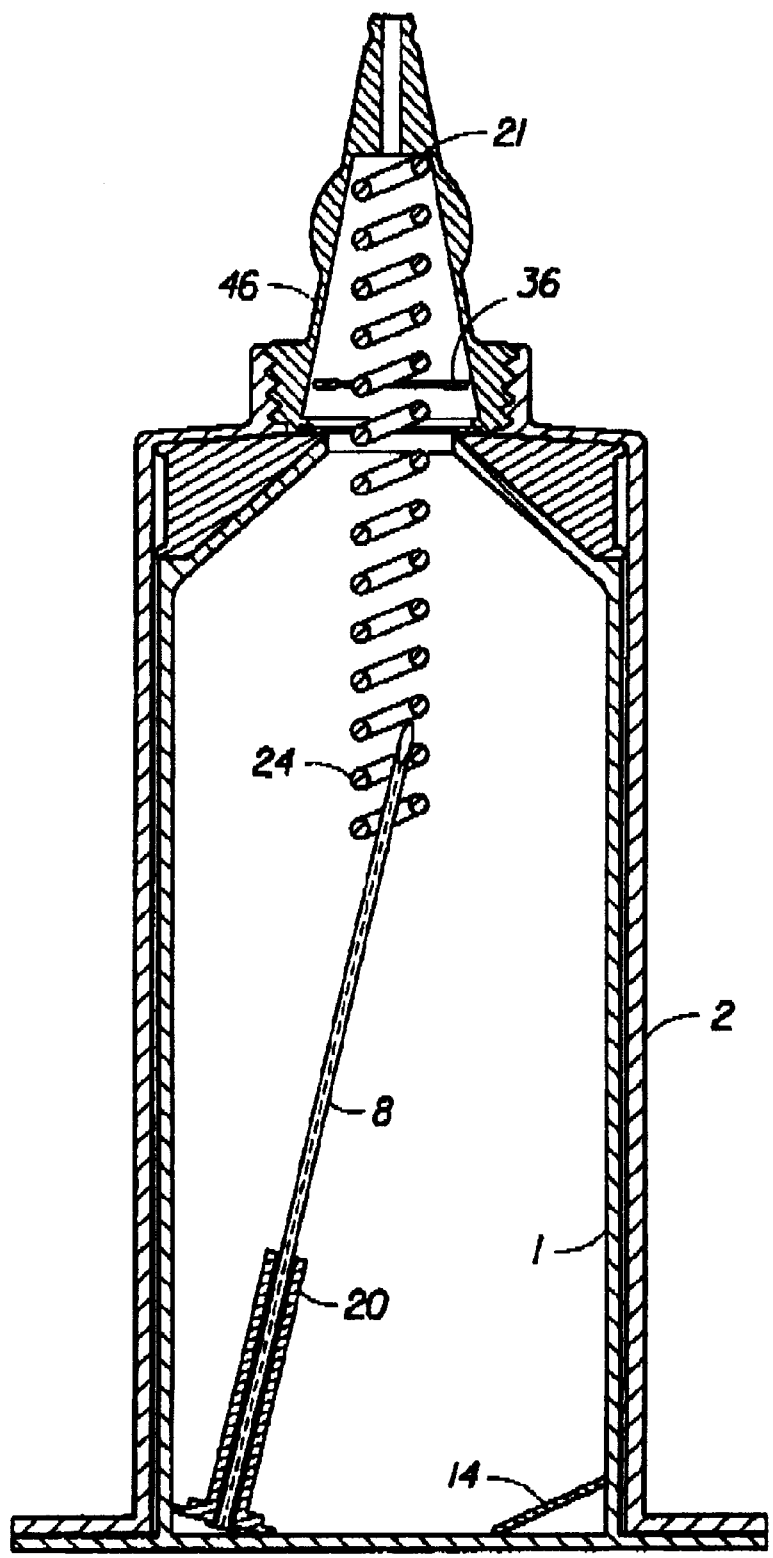
FIG. 10 is a section elevation of the safety needle cannula and the slideable piston inside of the safety plunger module.

FIG. 10 is a section elevation view of the needle cannula and slideable piston 20 having been retracted inside of the safety plunger 1. The biased spring 24 is now an relaxed, elongated spring 24. Optionally, the spring may be either loose or suitably fixed at the distal end to the cannula flat 21. The push in barrier 14 is shown as being separated from the end of the plunger and being inside the safety plunger 1, but it is anticipated that the barrier may remain partially attached to the end ridge.

Figure 11:
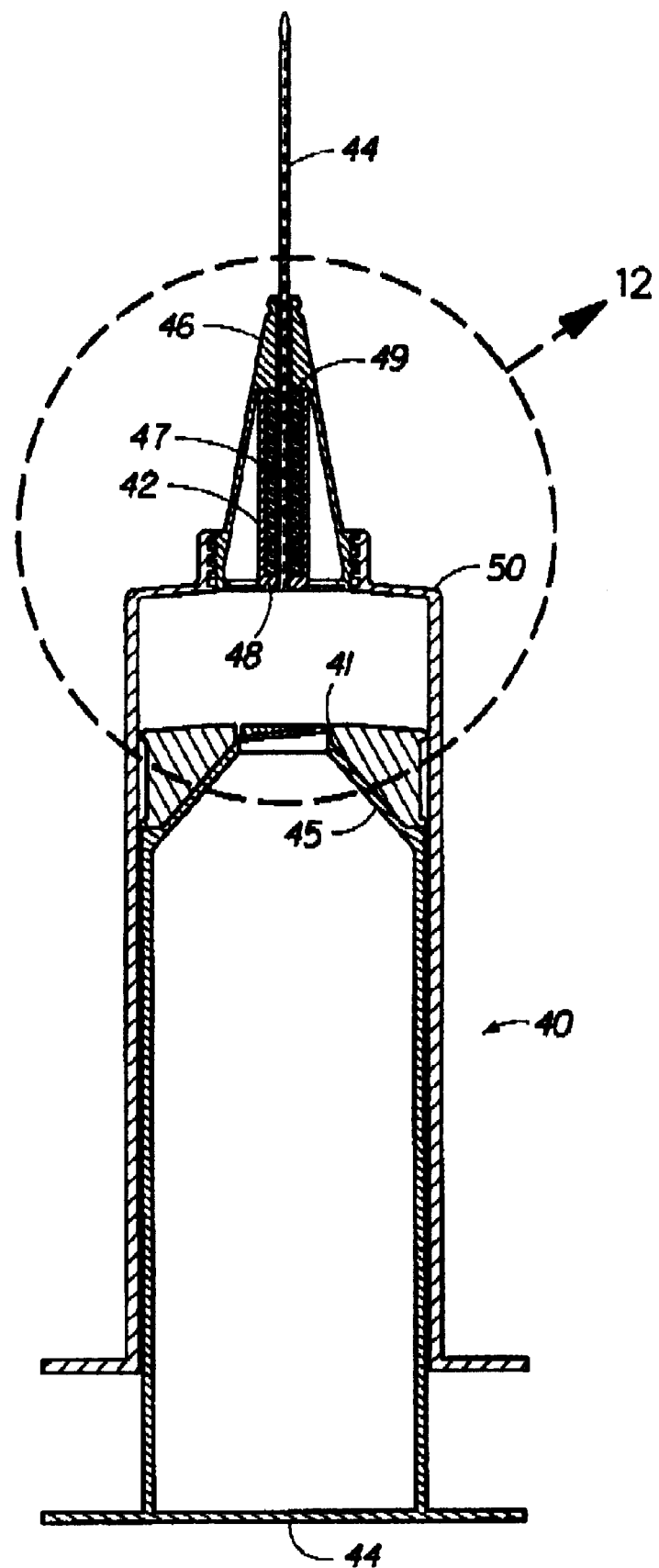
FIG. 11 is a section elevation of the safety needle of the second preferred embodiment.

FIG. 11 is a section elevation of the safety syringe 40 of a second preferred embodiment. There are two variations or differences between the safety syringe 40 of the second preferred embodiment and the safety syringe 12 of the first preferred embodiment. These variations include a sloping end ridge 41, a spring shield 42, and the elimination of the slideable piston.

The spring shield 42 is seen protecting the coiled biased spring 47 from catching anything that might impede the spring's ability to thrust the needle cannula shaft 44 all the way into the elongated hollow plunger 45. The spring shield 42 is contained in the safety cannula housing 46 with the distal end of the needle cannula shaft 44 extending out from the distal end of the safety cannula housing 46. A coiled, biased spring 47 is coiled about the needle cannula shaft 44. The proximal end of the coiled biased spring 47 pushes against the base plate 48 and the distal end of the coiled biased spring 47 pushes against the cannula flat 49. The syringe barrel 50 is shown as an elongated hollow barrel with an outside surface and an inside surface. The outside surface of the elongated hollow plunger 45 has an outer surface that is only slightly smaller than the inside surface of the syringe 50.

Figure 12:
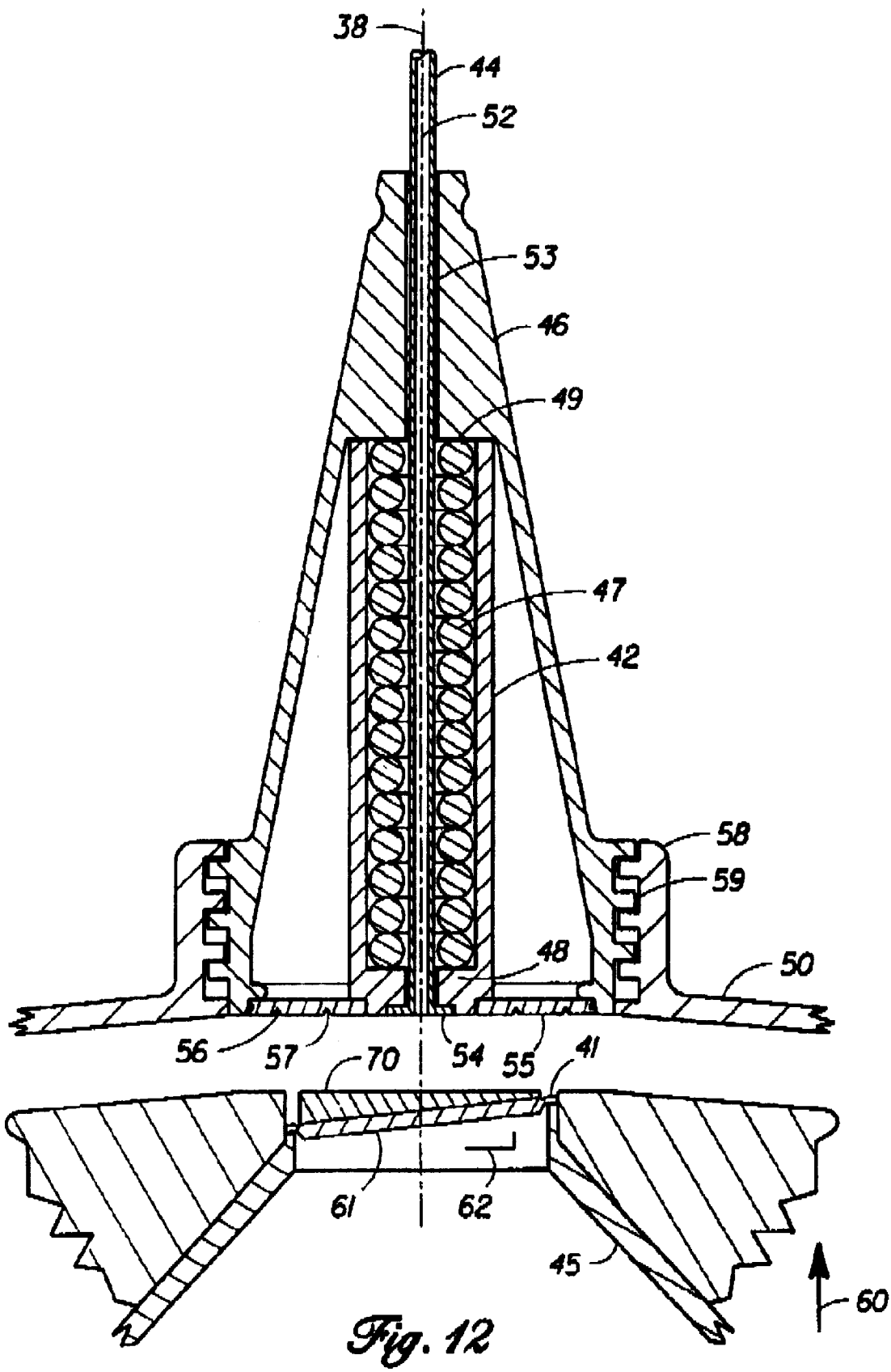
FIG. 12 is a section elevation of the first end of the plunger module with a slope.

FIG. 12 is an enlarged section elevation of the safety cannula housing 46. The needle cannula shaft 44 has a distal end terminating in a point, a proximal end and a cannula 52 formed on the inside of the needle cannula shaft 44. The needle cannula shaft 44 is shown with the distal end extending past the distal end of the safety cannula container 46, through the needle passage 53, through the coiled biased spring 47 wherein the proximal end of the needle cannula shaft 44 is suitably fixed to the base plate 48. The needle cannula shaft 44 may be fixed to the base plate 48 by adhesive, welding, friction or any other suitable means by design choice. The coiled biased spring 47 has a distal end biased against the needle flat 49 and a proximal end biased against the distal side of the base plate 48. The coiled biased spring 47 is contained by the needle cannula shaft 44 on the inside circumference of the coiled biased spring 47 and by the inside surface of the spring shield 42. The spring shield 42 is shown with the first end near or touching the needle flat 49. The proximal end of the spring shield 42 is shown fixed to the distal side of the base plate 48. The spring shield 42 is shown with the distal end near or touching the needle flat 49 to prevent any deflection or bending of the spring 47 or the needle cannula shaft 44. The needle flange 54 is shown suitably fixed to the proximal side of the base plate 48. The retaining member or shear plate 55 is shown with a first notch 56 and a second notch 57 wherein the shear plate 55 will withstand the maximum amount of hydraulic or pneumatic pressure that the syringe is designed to produce. However, when a point load or a concentrated load is applied to the shear plate 55 at a particular point, the shear plate 55 will fail at the first notch 56 and the second notch 57 or at another location on the shear plate 55.

The shear plate 55 is suitably secured to the base plate 48 on the inside with adhesive or some other suitable means, preferably forming a fluid tight barrier therebetween. The outside perimeter of the shear plate 55 is shown suitably fixed to the inside of the safety cannula housing 46 by adhesive or other suitable means, preferably forming a fluid tight barrier.

The safety cannula housing 46 is shown suitably fixed to the syringe connector 58 that is formed at the distal end of the syringe 50, preferably including threads 59 but optionally including any type connector.

Figure 13:
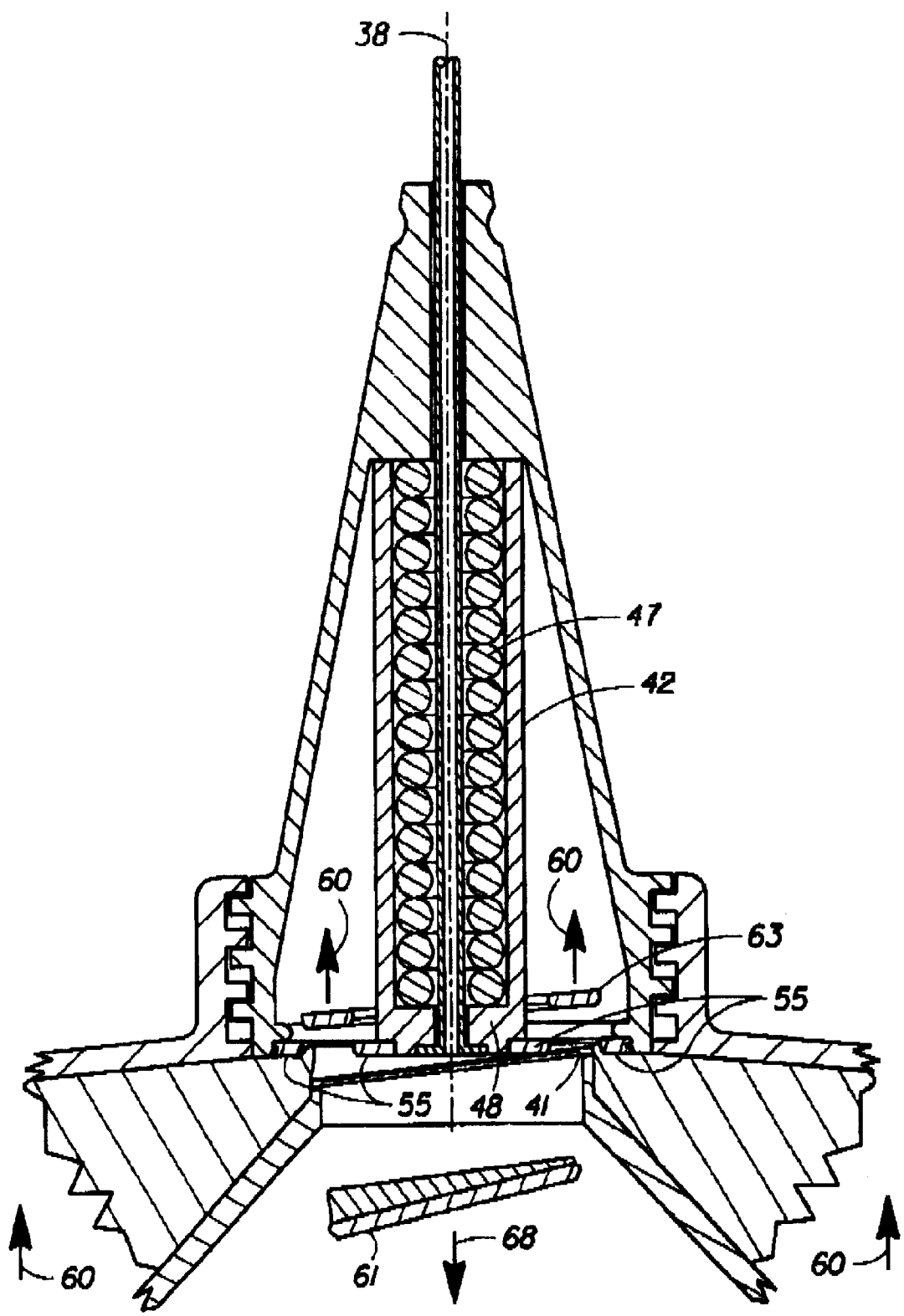
FIG. 13 is a section elevation of the sloping first end of the plunger module point loading the slideable piston barrier.
Figure 14:
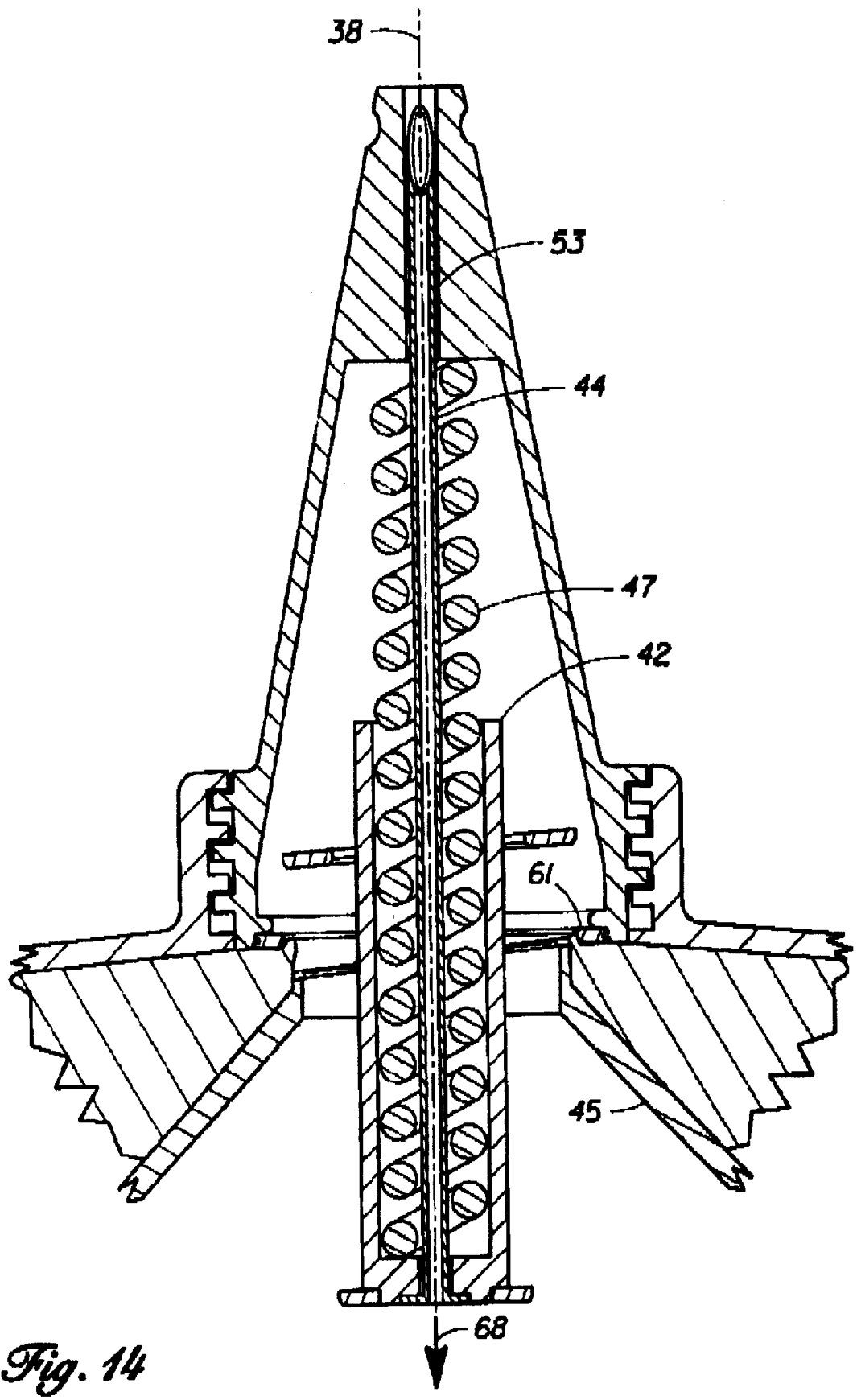
FIG. 14 is a section elevation of the needle and base plate thrusting into the plunger module.

The sloping end ridge 41 is shown near the shear plate 55. As the elongated hollow plunger 45 is pushed toward the needle cannula shaft 44 in a shear plate direction 60, the concentrated load plate 61 is shown with a slope 62 relative to the centerline 38. This slope 62 allows the sloping end ridge 41 to impact the shear plate 55 at only one point thereby exerting a point load on a small area, thereby initiating failure of the shear plate 55 and starting a progressive tearing process on the shear plate 55. The concentrated load plate 61 is thrust into a corner on the proximal side of the base plate 48 thereby exerting a concentrated load on the concentrated load plate 61, which load is in excess of the load that any hydraulic fluid would have applied during the operation of the safety syringe. In this manner, the concentrated load plate 61 will shear in one area and progressively tear away the entire outer periphery of the concentrated load plate 61 as the plunger 45 is thrust further toward the shear plate 55.

Where the concentrated load plate or other sealing member 61 is sloped, an optional spacer 70 may be used, preferably attached to the face of the member 61, to reduce or eliminate space in the syringe that will trap fluid therein. The spacer 70 is preferably made from a soft and easily compressible material to allow the FIG. 13 is an enlarged section elevation of the sloping end ridge 41 thrusting into the shear plate 55 in a shear plate direction 60. The break off ring 63 is now broken away from the shear plate 55. The corner of the base plate 48 is being pushed against by the concentrated load plate 61, causing the concentrated load plate 61 to progressively fail, tear or shear off of the sloping end ridge 41. The concentrated load plate 61 is shown moving in an inward direction 68. Because the end ridge does not protrude from the end of the plunger past the plunger gasket, the plunger gasket is shown as being somewhat compressed before the FIG. 14 is an enlarged section elevation of the needle cannula shaft 44 surrounded by the coiled biased spring 47 (in the process of unbiasing) and the spring shield 42 thrusting past the remainder of the shear plate 61 as the needle is thrusted into the elongated hollow plunger 45 in an inward direction 68.

Figure 15:
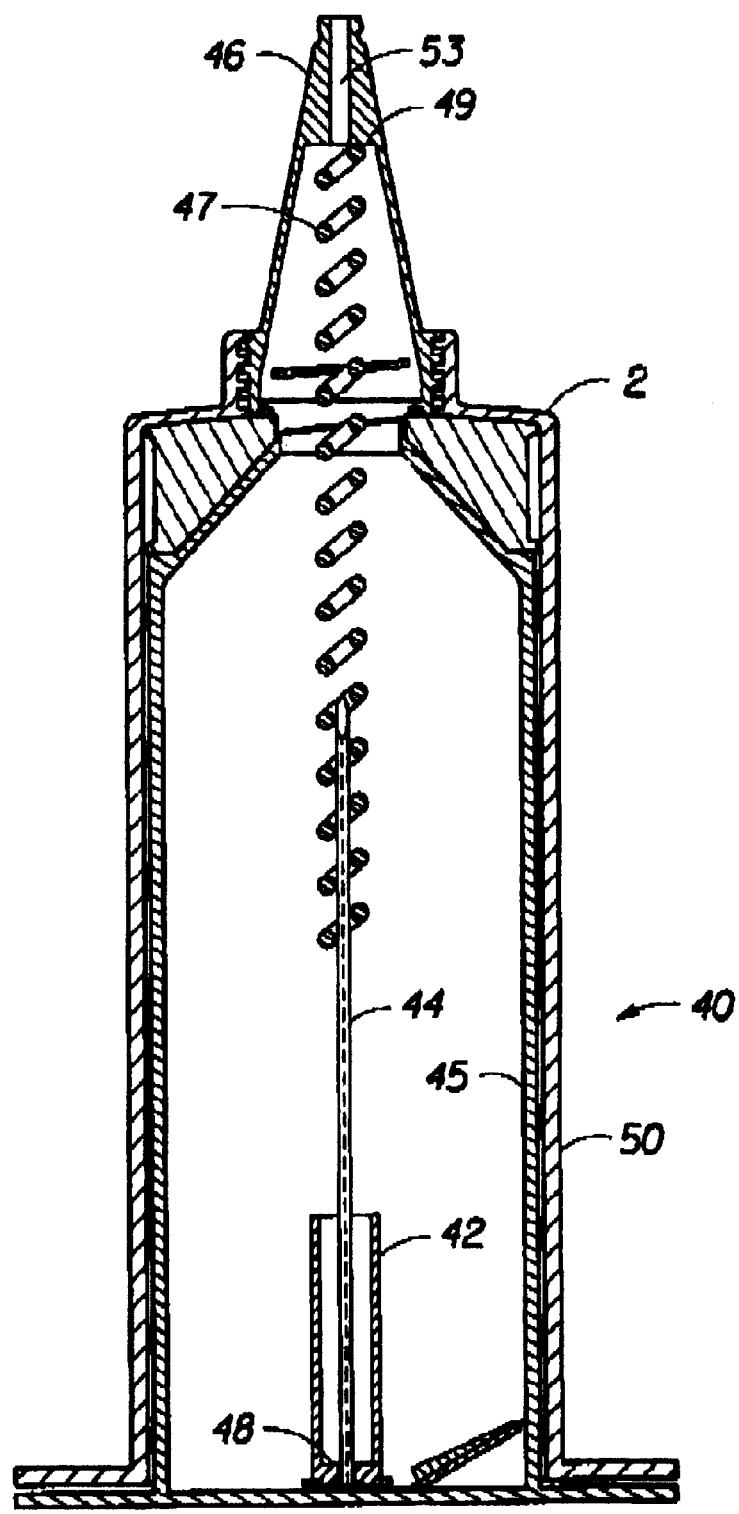
FIG. 15 is a section elevation of the needle, the spring shield and the base plate inside of the plunger.

FIG. 15 is a section elevation of the safety syringe 40 with the needle cannula shaft 44 safely in the elongated hollow plunger 45. The coiled spring 15 now unbiased is holding the needle cannula shaft 44 and the base plate 48 in the elongated hollow plunger 45. The needle cannula shaft 44 is now unable to come back out of the needle tunnel 53 to injure others or to be reused. There are other means of holding the elongated hollow plunger 45 inside of the syringe 50.

Figure 16:
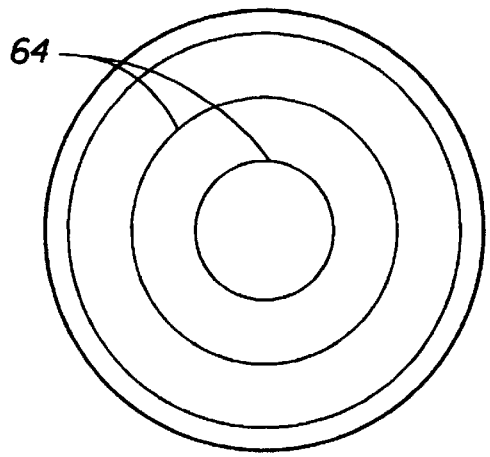
FIG. 16 is a plan view of the notches on the shear plate and concentrated load plate.
Figure 17:
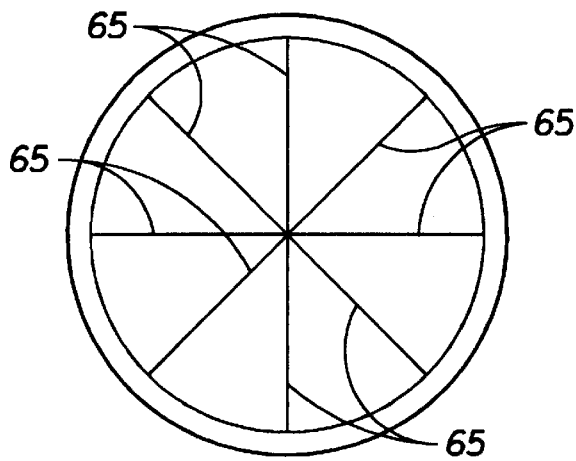
FIG. 17 is a plan view of the notches on the shear plate and concentrated load plate.
Figure 18:
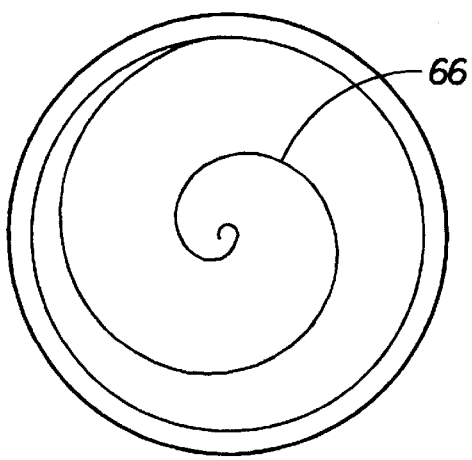
FIG. 18 is a plan view of the notches on the shear plate and concentrated load plate.
Figure 19:
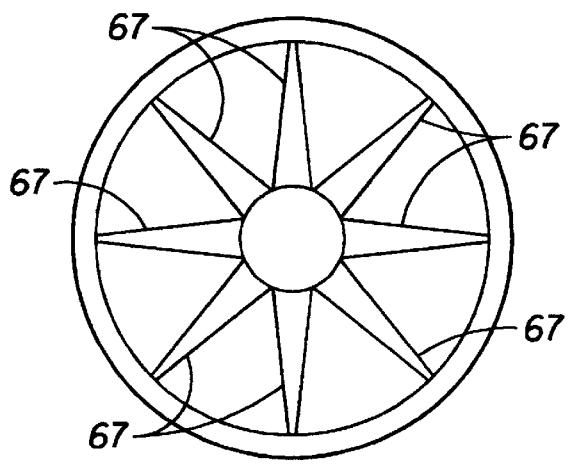
FIG. 19 is a plan view of the notches on the shear plate and concentrated load plate.

FIGS. 16, 17, 18 and 19 show various notch configurations suitable for use on either the shear plate 55 or the concentrated load plate 61. FIG. 16 has the notches forming concentric circles 64. FIG. 17 has radial notches 65. FIG. 18 has spiral notch(es) 66. FIG. 19 has star notches 67. There could be an infinite number of notch configurations by design choice.

Although the syringes and syringe systems described in detail above have been found to be most satisfactory and preferred, many variations are possible. For example the point load plate may not have notches in the first or second side, the point load plate may be square or rectangular, the concentrated load plate may be of various thicknesses or the safety needle cannula module may be axially offset.

Although the invention has been described with reference to the preferred embodiments, it will be understood by those skilled in the art, that additions, modifications, subtractions, deletions and other changes not specifically described, may be made in the embodiment herein. It should be understood that the details herein are to be interpreted as illustrations and are not in a limiting sense.

What is claimed is:

1. A kit of components for assembling safety syringes, comprising:
    (a) two or more safety syringe modules having different diameters, each safety syringe module having:
        (1) a syringe barrel;
        (2) a safety plunger extending through a proximal end of the syringe barrel, the safety plunger having a plunger barrel, a sliding gasket formed along the perimeter of the plunger barrel near the distal end for sealing the plunger against the interior sidewalls of the syringe barrel, a sealing member covering an opening in the distal end of the plunger barrel, and a rigid member adjacent the sealing member; and
        (3) a connector formed in the distal end of the syringe barrel;

(b) two or more safety needle cannula modules having:
  (1) a housing having a connector formed at a proximal end of the housing and a cannula passage formed through a distal end of the housing;
  (2) a needle cannula extending through the cannula passage;
  (3) a slidable piston flange coupled to the needle cannula;
  (4) a retaining member securing the slidable piston flange in the proximal end of the housing; and
  (5) a spring disposed within the housing to bias the slidable piston flange in the direction of the plunger opening from the distal end towards the proximal end;
(c) wherein the connectors in the two or more safety syringe modules are sealably securable to the connectors in the two or more safety needle cannula modules; and
(d) wherein securing any one of the two or more safety needle cannula modules to any one of the two or more safety syringe modules provides alignment of the rigid member of the plunger with the retaining member of the safety needle cannula module and alignment of the slideable piston flange with the sealing member of the plunger.

2. The kit of claim 1, wherein the rigid member of the plunger is an end ridge.

3. The kit of claim 2, wherein the end ridge is sloped.

4. The kit of claim 1, wherein the retaining element is selected from a shear plate, break plate, a friction ring, a sacrificial membrane, or a snapon ring.

5. The kit of claim 1, wherein the sealing member is selected from a break plate, a friction plug, a sacrificial membrane, a snapon plug.

6. The kit of claim 1, wherein the connectors are selected from threads, luer-loks, or snap-on fittings.

7. The kit of claim 1, wherein the needle cannulas of the two or more safety needle cannula modules are different sizes.

8. The kit of claim 1, wherein the plunger barrel narrows near the distal end to form the rigid member.

9. The kit of claim 8, wherein the plunger barrel narrows along a frustoconical surface.

10. The kit of claim 1, wherein the retaining element is selected from a shear plate or break plate and has first and second concentric notches formed therein, and wherein the rigid member is aligned to contact the retaining element between the first and second concentric notches.

* * * * *